United States Patent [19]

Revici

[11] Patent Number: 4,756,909

[45] Date of Patent: Jul. 12, 1988

[54] METHOD FOR RELIEVING PAIN OR PRODUCING ANALGESIA WITH N-BUTANOL

[75] Inventor: Emanuel Revici, New York, N.Y.

[73] Assignee: Elena Avram, New York, N.Y.

[21] Appl. No.: 99,453

[22] Filed: Sep. 21, 1987

Related U.S. Application Data

[62] Division of Ser. No. 856,905, Apr. 28, 1986, Pat. No. 4,695,583.

[51] Int. Cl.$^4$ ................. A61K 31/045; A61K 31/335; A61K 33/06
[52] U.S. Cl. .................................... 424/154; 514/449; 514/724
[58] Field of Search ....................... 514/721, 449, 724; 424/154

[56] References Cited

PUBLICATIONS

Quastel et al., Chem. Abstracts, vol. 105 (1986), #108400f.

Alifimoff et al., Chem. Abstracts, vol. 106 (1987), #131560n.

*Primary Examiner*—Stanley J. Friedman
*Assistant Examiner*—Richard Kearse
*Attorney, Agent, or Firm*—Pennie & Edmonds

[57] ABSTRACT

A method for treating a host for inducing relief of pain or anesthesia which comprises administering hydrolyzed epichlorohydrin, magnesium thiosulfate, or a butanol at the site of the painful area.

14 Claims, No Drawings

METHOD FOR RELIEVING PAIN OR PRODUCING ANALGESIA WITH N-BUTANOL

This is a division of application Ser. No. 856,905 filed Apr. 28, 1986, now U.S. Pat. No. 4,695,583.

TECHNICAL FIELD

This invention relates to methods and preparations for relieving pain or producing analgesia.

BACKGROUND ART

A number of methods exist for treating pain: an example being U.S. Pat. No. 3,898,325. The applicant has found a new method which is particularly effective for this purpose in compositions which are relatively simple to prepare and administer.

SUMMARY OF THE INVENTION

It has now been found that by administering various agents, such as hydroyzed epichlorohydrin (i.e., 1-chloro-2,3-epoxy propane), magnesium thiosulfate, or n-butanol directly to the painful area of a host will relieve the pain or produce analgesia therein.

DESCRIPTION OF THE INVENTION

It is known that the manifestation of pain is observed at the so-called trigger points. To successfully treat such pain, the administration of the compounds of the invention, preferably by injection, is found to control the pain in the immediate area as well as in the entire affected region.

One embodiment of the invention relates to the injection of from 1 to 10 ml of a solution of between 0.1 and 1.5 weight percent hydrolyzed epichlorohydrin at the trigger point or immediate painful area. The epichlorohydrin can be hydrolyzed by heating it in water. These amounts have been found to be advantageous, but can be higher or lower if desired. For example, up to 50 ml of a 0.5 weight percent solution can been used for exceptionally severe cases.

Generally, the pain is relieved in minutes following the injection. If necessary, the injections may be repeated, preferably 1-2 days later. If a stronger pain is present the next day at the site of the injection, this may be the result of an local inflammatory reaction. When this occurs, the pain usually disappears the day after, and the long term results are generally better.

Another approach for relieving pain is based upon the fact that pain generally has either an acid or alkaline pattern. This character is recognized through a relationship with the urinary pH: the acid pain being stronger with a lower pH and being weaker with a higher pH. The alkaline pains is just the opposite.

The acid pain corresponds to an anabolic imbalance with the predominant pathogenic action caused by steroids, while the alkaline pain corresponds to a catabolic action, with the predominant pathogenic action caused by fatty acids.

Many different agents can be used to counteract these imbalances. For the anabolic imbalances which are evidenced by acid pain, the injection of a solution of magnesium thiosulfate is utilized. The amount of this solution includes between about 10 and 50 ml of a water solution containing between about 10 and 50 weight percent magnesium thiosulfate.

For alkaline pain, which indicates a catabolic imbalance, a solution of butanol in water is used. The amount of this solution ranges from 5 to 25 ml of a solution of between about 5 and 10 weight percent butanol in water. Either n-butanol or sec-butanol can be used, with n-butanol preferred for best results. It is preferable to add to the butanol solutions about 25 to 50 percent by weight (based on the amount of butanol) of coramine (niketamide) for even better results.

As with the hydrolyzed epichlorohydrin solution, these solutions are preferably administered by injection. If the type of pain cannot be characterized as acid or alkaline, then the epichlorohydrin solution should be administered. It is also possible to use mixtures of these solutions.

When the nature of the disease which is causing the pain is known, more special agents, which can treat the disease or the symptoms of the disease, can be added to these solutions. Also, the number of injections can be repeated to enhance the pain reducing effect.

The preparations of the invention have practically no toxicity in the doses used.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A method for relieving pain or producing analgesia in a host having a painful area which comprises injecting n-butanol at the painful area in a sufficient amount to relieve pain and produce analgesia therein.

2. The method of claim 1 wherein the butanol is a solution comprising between about 5 and 10 weight percent n-butanol, balance water.

3. The method of claim 2 wherein the amount to be injected is between about 5 and 25 ml.

4. The method of claim 3 further comprising an effective amount of coramine or niketamide.

5. The method of claim 3 wherein the amount of coramine or niketamide comprises about 25 to 50 percent by weight of the amount of the butanol.

6. The method of claim 1 wherein the n-butanol to be administered further comprises an effective amount of magnesium thiosulfate.

7. The method of claim 6 wherein the magnesium thiosulfate is a solution comprising about 10 to 50 weight percent magnesium thiosulfate, balance water.

8. The method of claim 7 wherein the amount of magnesium thiosulfate solution to be injected is between about 10 and 50 ml.

9. A method for relieving pain or producing analgesia in a host having a painful area which comprises:
   injecting between about 5 and 25 ml of the solution comprising between about 5 and 10 weight percent n-butanol, balance water, at the painful area to relieve pain or produce analgesia therein.

10. The method of claim 9 wherein the n-butanol solution further comprises an effective amount of coramine or niketamide.

11. The method claim 9 wherein the amount of coramine or niketamide comprises about 25 to 50 percent by weight of the amount of the n-butanol.

12. The method of claim 9 wherein the n-butanol to be administered further comprises an effective amount of magnesium thiosulfate.

13. The method of claim 11 wherein the magnesium thiosulfate is a solution comprising about 10 to 50 weight percent magnesium thiosulfate, balance water.

14. The method of claim 13 wherein the amount of magnesium thiosulfate solution to be injected is between about 10 and 50 ml.

* * * * *